United States Patent
Yu

(10) Patent No.: US 8,361,536 B2
(45) Date of Patent: Jan. 29, 2013

(54) METHOD FOR FIXING ANTIBODY ON THE SURFACE OF MEDICAL INSTRUMENT

(75) Inventor: Zhanjiang Yu, Beijing (CN)

(73) Assignee: Lepu Medical Technology (Beijing) Co., Ltd., Beijing (CN)

( * ) Notice: Subject to any disclaimer, the term of this patent is extended or adjusted under 35 U.S.C. 154(b) by 587 days.

(21) Appl. No.: 12/593,110

(22) PCT Filed: Oct. 10, 2007

(86) PCT No.: PCT/CN2007/002916
§ 371 (c)(1),
(2), (4) Date: Nov. 3, 2009

(87) PCT Pub. No.: WO2008/141495
PCT Pub. Date: Nov. 27, 2008

(65) Prior Publication Data
US 2010/0112189 A1        May 6, 2010

(30) Foreign Application Priority Data
May 23, 2007   (CN) .......................... 2007 1 0107643

(51) Int. Cl.
*A61L 33/00*    (2006.01)
*A61M 25/00*    (2006.01)
*B05D 3/00*     (2006.01)

(52) U.S. Cl. ....... 427/2.1; 427/2.24; 427/2.25; 427/2.28
(58) Field of Classification Search .................. 427/2.1, 427/2.24, 2.25, 2.28
See application file for complete search history.

(56) References Cited

U.S. PATENT DOCUMENTS

| 2004/0078090 | A1  | 4/2004  | Binette et al. |
| 2006/0034884 | A1* | 2/2006  | Stenzel ........................ 424/422 |
| 2010/0254900 | A1* | 10/2010 | Campbell et al. ............ 424/1.65 |
| 2012/0114935 | A1* | 5/2012  | Schwartz et al. ............. 428/336 |
| 2012/0121661 | A1* | 5/2012  | Schwartz et al. ............. 424/400 |

FOREIGN PATENT DOCUMENTS

| CN | 1618472 | 5/2005 |
| CN | 1961978 | 5/2007 |

(Continued)

OTHER PUBLICATIONS

International Preliminary Report on Patentability (Chapter I of the Patent Cooperation Treaty) corresponding to International Patent Application No. PCT/CN2007/002916 dated Nov. 24, 2009.
International Search Report corresponding to International Patent Application No. PCT/CN2007/002916 dated Mar. 13, 2008.

(Continued)

Primary Examiner — Timothy Vanoy
(74) Attorney, Agent, or Firm — Jenkins, Wilson, Taylor & Hunt, P.A.

(57) ABSTRACT

A method for fixing antibody on the surface of medical instrument, mainly includes: 1) pre-treating the instrument surface; 2) preparing holes: preparing multicrystal phase structure which has same size holes in the surface of the instrument by chemical corrosion, electrochemical corrosion, anodic oxidation, micro-arc oxidation, micro-arc nitridation; 3) post-treating the instrument surface; 4) fixing the antibody: immerging the bare metal scaffold which has holes in surface into a buffer solution containing antibody, adjusting the pH value of the antibody buffer solution, fixing the antibody on the surface of the instrument by the attraction between positive and negative charge and hole effect; and 5) confirming the effectiveness of the fixed antibody by artificial simulation hemodynamics and detecting method of antibody activity in scaffold surface.

11 Claims, 4 Drawing Sheets

FOREIGN PATENT DOCUMENTS

| | | |
|---|---|---|
| CN | 200980747 | 11/2007 |
| CN | 200980748 | 11/2007 |
| WO | WO2004112863 | 12/2004 |
| WO | WO2008/141495 | 11/2008 |

OTHER PUBLICATIONS

Written Opinion corresponding to International Patent Application No. PCT/CN2007/002916 dated Mar. 13, 2008.

* cited by examiner

METHOD FOR FIXING ANTIBODY ON THE SURFACE OF MEDICAL INSTRUMENT

TECHNICAL FIELD

The present invention belongs to the field of medical instrument, and relates to a method for fixing antibody on the surface of medical instrument.

BACKGROUND

It has been widely applied to biochip to fix biological products, such as protein, antibody, growth factor and gene plasmid, on the solid surfaces, such as the surface of metal, ceramics and polymeric material. As the development of medical instruments, especially the emergence of drug-containing medical instrument, fixing biological products on the surface of the medical instrument has become an extensive and in-depth issue. Comparing with common protein, the antibody contained in biological product has advantages such as high stability, hard inactivation and specificity of antigen-antibody reaction and has been widely used as in vitro diagnostic reagent and has been applied to medical diagnosis. Thus, the method for firmly fixing the antibody on the surface of the medical instrument including the surface of metal and various surface of polymeric coatings without damaging the activity of the antibody has become a key scientific and technological technique.

Nowadays, the method for fixing the antibody on the solid surface generally includes chemical bonding and physical adsorption. The method of chemical bonding generally includes the steps of forming aldehyde group and carboxy group on the solid surface firstly and fixing the antibody by chemical grafting. Two key points call for solution when fixing the antibody on the solid surface: 1 firm degree of the antibody which is fixed on the solid surface; 2 the maintenance of the activity of the antibody on the solid surface. For the biochip, the most commonly used method is to form aldehyde group and carboxy group on the solid surface, such as the surface of glass, metal and plastic firstly and then fix the antibody on the solid surface by chemical grafting. This method has advantages of high firm degree for fixing the antibody well, but can reduce the activity of the antibody to a certain extent. The method of physical adsorption is simple and able to keep good activity of the antibody on the solid surface, but is hard to maintain the firm degree of the fixed antibody. Thus, how to fix these biological products on the surface of the medical instrument remains a key technical problem left to be solved.

CONTENTS OF THE INVENTION

The object of the present invention is to provide a method for fixing antibody on the surface of medical instrument, which may improve the firm degree of the antibody which is fixed on the surface of medical instrument and keep high activity of antibody on the surface of the medical instrument.

The technical solution of the present invention is as follows: a method for fixing antibody on the surface of medical instrument, mainly includes ① pre-treating the instrument surface, ② preparing holes, ③ post-treating the instrument surface and ④ fixing the antibody; first, preparing multicrystal phase structure which has same size holes in the surface of the instrument by chemical corrosion, electrochemical corrosion, anodic oxidation, micro-arc oxidation, micro-arc nitridation; and then immersing the bare metal scaffold which has holes in surface into a buffer solution containing antibody, adjusting the pH value of the antibody buffer solution, fixing the antibody on the surface of the instrument by the attraction between positive and negative charge and physical adsorption effect of holes; finally, confirming the effectiveness of the fixed antibody by artificial simulation hemodynamics and detecting method of antibody activity in the scaffold surface.

The step ① pre-treating the instrument surface includes: washing the instrument surface by ultrasonic to remove impurities, using 99.5% concentration of analytical reagent acetone solution or 75% concentration of medical ethanol solvent to wash the scaffold body material for 5~15 min by 28~100 khz ultrasonic to remove the impurities on the body material, putting the washed body material into a dryer to dry for 30~60 min at 30~40° C., and then taking out the body material left to be used.

The step ② preparing holes includes: directly preparing holes with the same size in the instrument by acid solution corrosion; immerging the instrument material into the 0~100° C. corrosion solution; and the corrosion solution is preferably hydrochloric acid at concentration of 1~38% or the hydrochloric acid mixed acid solution with 1~38% hydrochloric acid mixed with 1~98% vitriol; and then forming single nanometer-size holes by corrosion for 1 min~480 h; and the corrosion time varies according to the concentration and temperature.

The step ③ post-treating the instrument surface includes: using 99.5% concentration of analytical reagent acetone solution and distilled water in sequence to wash the body material for 5~15 min using 28~100 khz ultrasonic; and finally putting the washed body material into a dryer to dry for 30~60 min at 30~40° C., and then taking out the body material left to be used, or preparing 1~38% concentration of hydrochloric acid solution with distilled water and then immerging the body material into the prepared solution and putting the solution containing the body material into an incubator at 20° C. and then taking out the body material after 30 min~48 h.

The instrument includes scaffold, catheter, guide wire, heart pacemakers, heart valves, surgical implant materials, implant hard tissue, and non-metal medical instrument whose substrate is ceramics, organic polymer, inorganic substance or metal oxide; the scaffold is balloon-expandable, self-expanding, vessel or non-vessel stent, stent whose substrate is stainless steel, nickel-titanium memory alloy, cobalt-based alloy, titanium or titanium alloy; and the scaffold made by wire weaving, tube laser cutting, die casting or welding.

The biological product antibodies include one or more of the following substances: heparin, anti-platelet membrane glycoprotein (GPIIb/IIIa) receptor antagonists, antibody-treating cancer drug, abciximab, biological peptides, CD34 antibody, CD31 antibody and CD133 antibody.

The step ④ fixing the antibody includes:

(1) immerging the scaffold which has holes in surface into the phosphate buffer solution or the carbonate buffer solution containing 0.1~100 µg/mL CD34 antibody to incubate for 20~60 min at 25~37° C. and then taking out the scaffold;

(2) washing the scaffold 3 times for 5 min per time using the phosphate buffer solution and blowing the scaffold for 15 min at room temperature and then preserving the scaffold at 4° C. after it becomes dry.

Conducting step ⑤ directly detecting the antibody activity after fixing the antibody includes: performing fluorescence coloring through the specific reaction of CD34 antigen-antibody using fluorescein isothiocyanate (FITC) labeled mouse anti-human CD34 antibody and detecting the antibody activity on the scaffold surface by photo-detection of fluorescence using fluorescence microscope.

(1) immerging the scaffold which has antibody on surface into the phosphate buffer solution containing 500 μL 5~10% bovine serum albumin (BSA) to incubate for 30 min~2 h at 25~37° C. and then taking out the scaffold to dry in the air;

(2) immerging the scaffold which has antibody on surface into the phosphate buffer solution containing 500 μL 0.01~10 ng/μL human recombinant CD34 antigen for 30 min~2 h at 25~37° C. and then taking out the scaffold to dry in the air;

(3) immerging the scaffold into the phosphate buffer solution containing 500 μL 1 μg/mL fluorescein isothiocyanate (FITC) labeled CD34 antibody to incubate for 20~30 min at 25~37° C. and then taking out the scaffold;

(4) washing the scaffold 3 times for 5 min per time with the phosphate buffer solution and then drying the scaffold;

(5) observing the scaffold surface for fluorescence under the fluorescence microscope (the bare metal scaffold as a control at the same time).

After the step (4) fixing the antibody, step (6) indirectly detecting the antibody activity is conducted: detecting the antibody activity on the scaffold surface with 3-amino-9-ethyl-carbazole (AEC) staining kit after cascade amplification of goat anti-mouse IgG secondary antibody labeled by horseradish peroxidase (HRP).

After the step (4) fixing the antibody, step (6) indirectly detecting the antibody activity includes:

(1) immerging the scaffold which has antibody on surface into the phosphate buffer solution containing 500 μL 5~10% bovine serum albumin (BSA) to incubate for 30 min~2 h at 25~37° C. and then taking out the scaffold to dry in the air;

(2) immerging the scaffold into the phosphate buffer solution containing horseradish peroxidase (HRP) labeled goat anti-mouse IgG to incubate for 20~30 min at 25~37° C. and then taking out the scaffold;

(3) washing the scaffold 3 times for 5 min per time by the phosphate buffer solution;

(4) using 3-amino-9-ethyl-carbazole (AEC) staining kit produced by China Huamei Bio-engineering Corporation, after immunohistochemical staining taking a photograph of the scaffold, and using the 316L stainless steel stent with holes as a control.

After the step (4) fixing the antibody, step (7) detecting the content of the antibody on surface is conducted: indirectly detecting the content of the antibody on the scaffold surface by tetramethylbenzidine (TMB) chromogenic after cascade amplification of horseradish peroxidase (HRP) labeled goat anti-mouse IgG secondary antibody.

After the step (4) fixing the antibody, step (7) detecting the content of the antibody on surface includes:

(1) immerging the scaffold which has antibody on surface into the phosphate buffer solution containing 500 μL 5~10% bovine serum albumin (BSA) to incubate for 30 min~2 h at 25~37° C. and then taking out the scaffold to dry in the air;

(2) immerging the scaffold into the phosphate buffer solution containing horseradish peroxidase (HRP) labeled goat anti-mouse IgG to incubate for 20~30 min at 25~37° C. and then taking out the scaffold;

(3) washing the scaffold 3 times for 5 min per time by the phosphate buffer solution; putting the scaffold into 500 μL TMB substrate buffer solution; the 500 μL TMB substrate buffer solution is made of, such as, 0.5 mL anhydrous ethanol of 10 mg/5 mL mixed with 5 mL substrate buffer solution; the substrate buffer solution is made of, such as, 1.42 g $Na_2HPO_4$ mixed with 0.96 g sodium citrate which is added distilled water to 50 mL; after washing, adding 32 μL hydrogen peroxide of 0.75% into the phosphate buffer solution to incubate for 15 minutes and then adding 250 μL 2 M sulfuric acid solution to stop the reaction;

(4) using the microplate reader to measure the absorbance of the solution at 492 nm;

(5) coating the mouse anti-human CD34 antibody having a known concentration on an ELISA plate according to the different concentration gradients of 1:10, 1:20, 1:50, 1:100, 1:500, 1:1000, 1:10000 and 1:50000, and conducting steps (1) to (4) at the same time, and then drawing a standard curve by simulation of the concentration of CD34 antibody with the absorbance of the solution at 492 nm.

(6) determining the amount of the antibody on the scaffold surface according to the measured absorbance of and the standard curve; the result showed that 316L stainless steel stent with holes can fix 1~20 ng CD34 antibody each 1 mm in length.

After the step (4) fixing the antibody, step (8) detecting the firm degree of the antibody is conducted: putting the scaffold with the fixed mouse anti-human CD34 antibody on surface into fluid artificial simulated body fluid, such as the phosphate buffer solution, whose pressure is 100 mmHg and flow rate is 91 cm/s, performing a scouring experiment, when the scaffold is in a normal state or in a state after the balloon dilation; finally, using the method step (6) described to detect the antibody activity on the scaffold surface and using the method of step (7) to quantify the antibody on the scaffold.

The beneficial effects of the present invention include:

1. It forms the surface with holes which have same size and the multicrystal phase structure in the surface of the medical instrument by chemical corrosion, electrochemical corrosion; the biological product antibody is fixed on the surface of the medical instrument by the effect of physical adsorption with a high firm degree for keeping high activity of the antibody on the surface of the medical instrument.

2. The formation of the holes makes it possible to fix the biological product antibody on the surface of the medical instrument well and thus gives full play to the role of the biological products in the prevention of in-stent restenosis and antithrombotic and overcomes the negative impacts brought about by the medical instrument during use, such as in-stent restenosis and formation of antithrombotic, to bring gospel for patients with coronary atherosclerosis.

3. The present invention has simple processes and accurate and reliable detection results, which can be widely applied to biochip and the surface of the medical instrument, such as vessel stents and orthopedic implant devices, for fixing the biological antibody.

DETAILED MODE OF CARRYING OUT THE INVENTION

Figure 1:
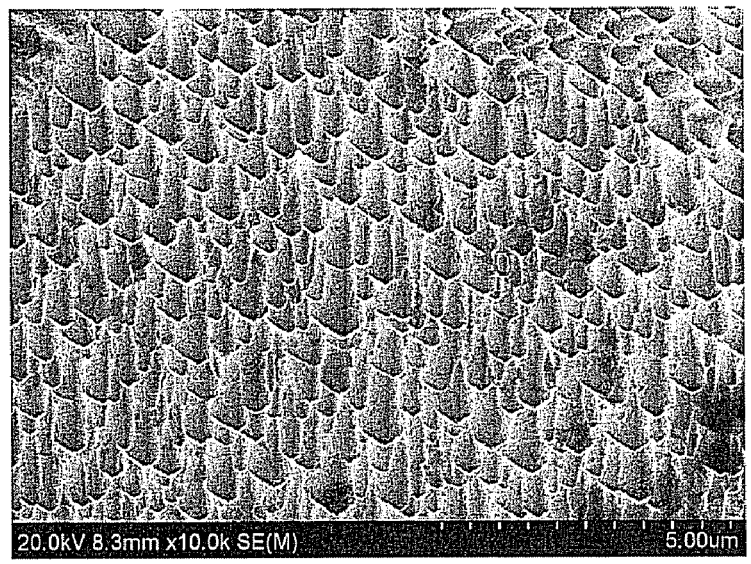
FIG. 1 illustrates the scanning electron microscope photo of the treated surface of 316L stainless steel stent of the invention.

A method for fixing antibody on the surface of medical instrument, mainly includes ① pre-treating the instrument surface, ② preparing holes, ③ post-treating the instrument surface, ④ fixing the antibody, and ⑤ detecting the antibody activity, etc; first, preparing the surface which has holes with the same size 100~1000 nm and multicrystal phase structure in the surface of the medical instrument, such as the 316L stainless steel bare metal scaffold by chemical corrosion, electrochemical corrosion, anodic oxidation, micro-arc oxidation, micro-arc nitridation. As shown in FIG. 1, it is the scanning electron microscope photo of the processed surface of 316L stainless steel stent, wherein:

① pre-treating the instrument surface: washing the surface of the instrument such as stainless steel bare scaffold by ultrasonic to remove impurities, using analytical reagent acetone solution at a concentration of 99.5% or medical ethanol solvent at a concentration of 75% to wash the scaffold body material for 5~15 min using 28~100 khz ultrasonic to remove the impurities on the body material, putting the washed body material into a dryer to dry for 30~60 min at 30~40° C., and then taking out the body material left to be used.

② preparing holes: directly preparing holes with the same size in the instrument by acid solution corrosion; immersing the instrument material into the 0~100° C. corrosion solution; and the corrosion solution is preferably hydrochloric acid at concentration of 1~38% or the hydrochloric acid mixed acid solution containing 1~38% hydrochloric acid mixed with 1~98% vitriol; and then forming single nanometer-size holes after corrosion for 1 min~480 h; and the corrosion time varies according to the concentration and temperature.

③ post-treating the instrument surface: using 99.5% concentration of analytical reagent acetone solution and distilled water to wash the body material for 5~15 min in succession by 28~100 khz ultrasonic; and finally putting the washed body material into a dryer to dry for 30~60 min at 30~40° C., and then taking out the body material left to be used, or preparing 1~38% concentration of hydrochloric acid solution with distilled water and then immersing the body material into the prepared solution and putting the solution containing the body material into an incubator at 20° C. and then taking out the body material after 30 min 48 h.

④ fixing the antibody: immersing the bare metal scaffold which has holes in surface into a buffer solution containing antibody, adjusting the pH value of the antibody buffer solution, fixing the antibody on the surface of the instrument by the attraction between positive and negative charge and hole effect, and promoting the firm degree of the antibody fixed on the surface of the instrument by the depth and size of the holes in the surface of the bare metal scaffold. The method can fix the antibody firmly and keep high activity of the antibody on the scaffold surface;

⑤ detecting the antibody activity: confirming the effectiveness of the fixed antibody by artificial simulation hemodynamics and detecting method of antibody activity in the scaffold surface.

The instrument includes scaffold, catheter, guide wire, heart pacemakers, heart valves, surgical implant materials, implant hard tissue, and non-metal medical instrument whose substrate is ceramics, organic polymer, inorganic substance or metal oxide; the scaffold is balloon-expandable, self-expanding, vessel or non-vessel stent whose substrate is stainless steel, nickel-titanium memory alloy, cobalt-based alloy, titanium or titanium alloy; and the scaffold is made by wire weaving, tube laser cutting, die casting or welding.

The biological product includes one or more of the following substances: heparin, anti-platelet membrane glycoprotein (GPIIb/IIIa) receptor antagonists, antibody-treating cancer drug, abciximab, biological peptides, CD34 antibody, CD31 antibody and CD133 antibody.

Hereafter the preferable examples of the present invention will be given:

Example 1

The method of fixing antibody CD34 on the scaffold surface based on the antigen-antibody binding reaction and the fluorescence detection of the antibody activity have the steps as follows:

(1) immerging the 316L stainless steel stent which has holes in surface into the phosphate buffer solution or the carbonate buffer solution, whose pH is 7.2~7.4, containing 0.1~100 μg/mL CD34 antibody such as type Ilmouse anti-human CD34 antibody produced by U.S. Stem Cell Technology Co., Ltd., to incubate for 30 min~2 h at 25~37° C. and then taking out the scaffold;

(2) washing the scaffold 3 times for 5 min per time using the phosphate buffer solution, whose pH is 7.2~7.4, and blowing the scaffold for 15 min at room temperature 25° C. and then preserving the scaffold at 4° C. after it becomes dry.

Figure 2:
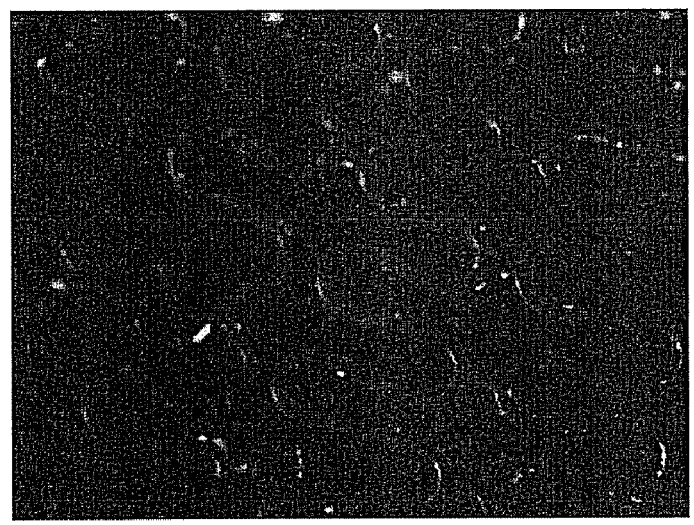
FIG. 2 illustrates the fluorescent photo of the scaffold with antibody of the invention.

(3) immerging the scaffold which has antibody on surface into the phosphate buffer solution, whose pH is 7.2~7.4, containing 500 μL 5~10% bovine serum albumin (BSA) to incubate for 20~30 min at 25~37° C. and then taking out the scaffold to dry in the air;

(4) immerging the scaffold which has antibody on surface into the phosphate buffer solution, whose pH is 7.2~7.4, produced by U.S. biology company containing 500 μL 0.01~10 ng/μL human recombinant is CD34 antigen for 20~30 min at 25~37° C. and then taking out the scaffold to dry in the air;

(5) immerging the scaffold into the phosphate buffer solution, whose pH is 7.2~7.4, containing 500 μL 1 μg/mL fluorescein isothiocyanate (FITC) labeled CD34 antibody such as type Ilmouse anti-human CD34 antibody produced by U.S. Stem Cell Technology Co., Ltd. to incubate for 20~30 min at 25~37° C. and then taking out the scaffold;

(6) washing the scaffold 3 times for 5 min per time by the phosphate buffer solution, whose pH is 7.2~7.4, and then drying the scaffold;

(7) taking fluorescence photography of the scaffold using fluorescence microscope, such as Japan CKX41-A32PH/FL Olympus fluorescence microscope and using the 316L stainless steel stent with holes as a control stent with the result shown in FIG. 2.

Example 2

Figure 3:
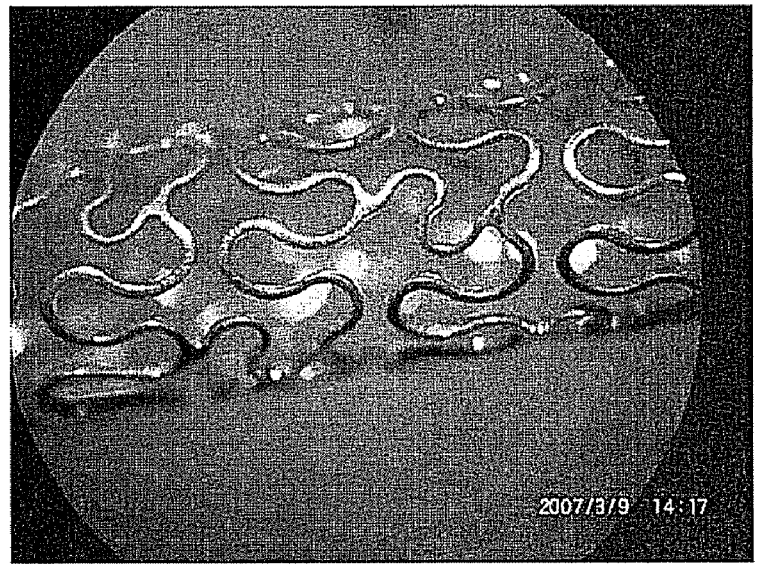
FIG. 3 illustrates 3-amino-9-ethyl-carbazole (AEC) staining photo of the 316L stainless steel stent with holes of the invention.
Figure 4:
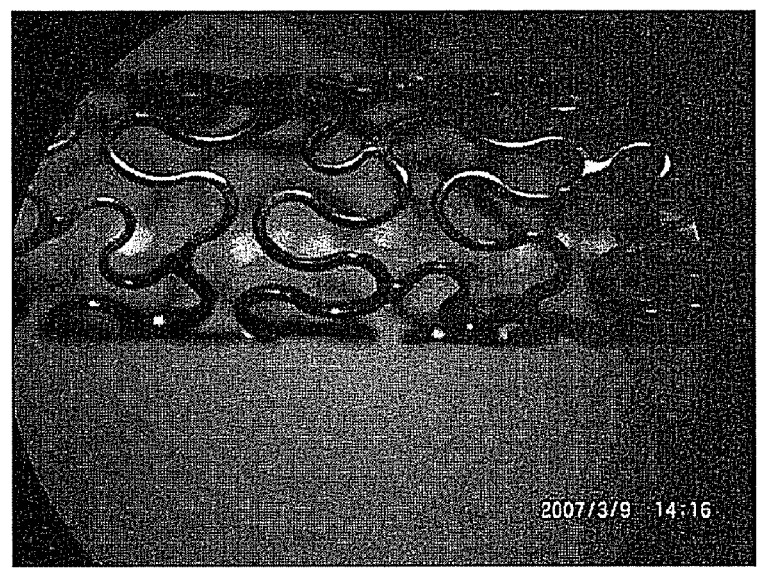
FIG. 4 illustrates 3-amino-9-ethyl-carbazole (AEC) staining photo of the scaffold with antibody of the invention.

The method of fixing antibody CD34 on the scaffold surface based on the antigen-antibody binding reaction and the immunohistochemistry detection of the antibody activity, and the method of fixing antibody CD34 on the scaffold surface is the same as the steps 1 and 2 disclosed in example 1;

(3) immerging the scaffold which has antibody on surface into the phosphate buffer solution containing 500 μL 5~10% bovine serum is albumin (BSA) to incubate for 30 min~2 h at 25~37° C. and then taking out the scaffold to dry in the air;

(4) immerging the scaffold into the phosphate buffer solution containing horseradish peroxidase (HRP) labeled goat anti-mouse IgG to incubate for 20~30 min at 25~37° C. and then taking out the scaffold;

(5) washing the scaffold 3 times for 5 min per time by the phosphate buffer solution;

(6) after using 3-amino-9-ethyl-carbazole (AEC) staining kit produced by China Huamei Bio-engineering Corporation for immunohistochemical staining, taking a photograph of the scaffold, and using the 316L stainless steel stent with holes as a control with the result shown in FIG. 3 and FIG. 4.

Example 3

Figure 5:
FIG. 5 illustrates the staining result of the scaffold with antibody before it is preinstalled after being scoured for 24 h of the invention.
Figure 6:
FIG. 6 illustrates staining result of the scaffold with antibody after scoured for 24 h after the balloon dilation of the invention.

The steps of hemodynamics simulation experiment of scaffold with antibody in artificial body flow, the method of fixing the antibody on the scaffold surface and the firm degree detection are as follows:

(1) putting the scaffold with the fixed mouse anti-human CD34 antibody on surface into fluid artificial simulated body flow, such as the phosphate buffer solution, whose pressure is 100 mmHg, flow rate is 91 cm/s and pH is 7.2~7.4, to make a scouring experiment, when the scaffold is at a normal state or at a state after the balloon dilation;

(2) after the scaffold surface is scoured for 24 hours, detecting the activity of the antibody on the scaffold surface with the method disclosed in Example 2; the experimental results are shown in FIG. 5 and FIG. 6, which indicate that the method of absorbing the antibody using the holes in the surface of the scaffold has the advantage of high firm degree, and enables the antibody to be fixed on the scaffold surface even in the arterial blood flow in high-speed and to keep high activity.

Example 4

It is the method of fixing the antibody on the scaffold surface and the quantitative detection of the antibody after being cascade amplified, and the steps thereof are as follows:

(1) immerging the 316L stainless steel stent which has holes in surface into the phosphate buffer solution, whose pH is 7.2~7.4, containing 0.1~10 μg/mL CD34 antibody such as type II mouse anti-human CD34 antibody produced by U.S. Stem Cell Technology Co., Ltd. to incubate for 30 min~2 h at 25~37° C. and then taking out the scaffold;

(2) washing the scaffold 3 times for 5 min per time using the phosphate buffer solution, whose pH is 7.2~7.4, and blowing the scaffold for 15 min at room temperature 25° C. and then preserving the scaffold at 4° C. after it becomes dry.

(3) immerging the scaffold which has antibody on surface into the phosphate buffer solution, whose pH is 7.2~7.4, containing 500 μL 5~10% bovine serum albumin (BSA) to incubate for 20~30 min at 25~37° C. and then taking out the scaffold to dry in the air;

(4) immerging the scaffold into the phosphate buffer solution containing horseradish peroxidase (HRP) labeled goat anti-mouse IgG produced by China Huamei Bio-engineering Corporation to incubate for 20~30 min at 25~37° C. and then taking out the scaffold;

(5) washing the scaffold 3 times for 5 min per time by the phosphate buffer solution; the step of washing is putting the scaffold into 500 μL TMB substrate buffer solution; the 500 μL TMB substrate buffer solution is made of, such as, 0.5 mL anhydrous ethanol of 10 mg/5 mL mixed with 5 mL substrate buffer solution; the substrate buffer solution is made of, such as, 1.42 g $Na_2HPO_4$ mixed with 0.96 g sodium citrate which is added distilled water to 50 mL; after washing, adding 32 μL hydrogen peroxide of 0.75% into the phosphate buffer solution to incubate for 15 minutes and then adding 250 μL 2 M sulfuric acid solution to stop the reaction;

(6) using the microplate reader to measure the absorbance of the solution (A492), taking the 316L stainless steel stent with holes as a control, coating CD34 antibody having a known concentration on an ELISA plate according to the different concentration gradients of 1:10, 1:20, 1:50, 1:100, 1:500, 1:1000, 1:10000 and 1:50000 at the same time, and detecting A492 nm according to the above mentioned methods, and then making a simulation of the concentration of CD34 antibody with A492 nm to draw a standard curve.

(7) determining the quantities of the antibody on the scaffold surface according to the absorbance of the measured solution and the standard curve; the result showed that 316L stainless steel stent with holes can fix 1~20 ng CD34 antibody for each 1 mm in length.

Example 5

Figure 7:
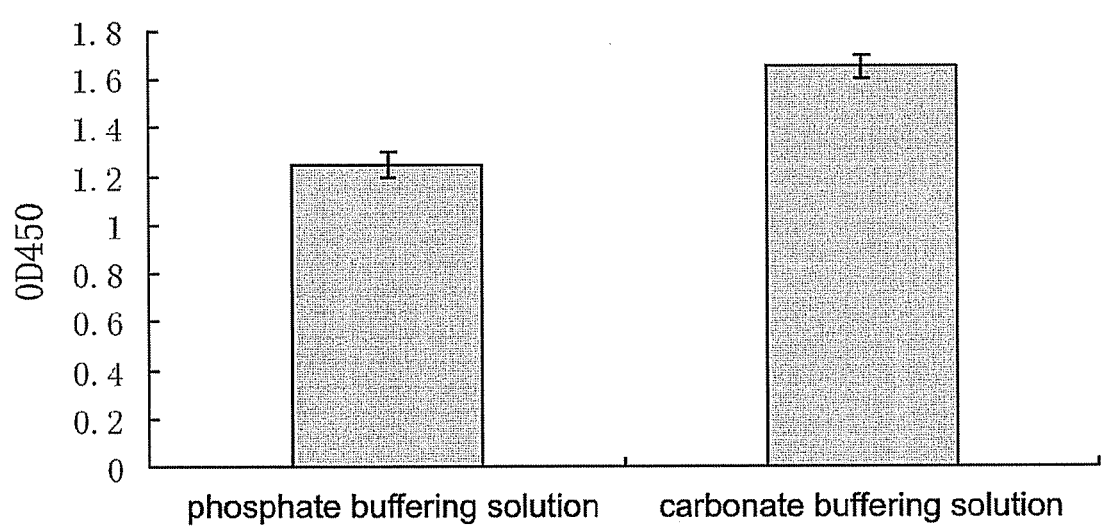
FIG. 7 illustrates the control of the relative contents of antibodies fixed with the holes under different craft conditions of the invention.

In order to detect the impact of the relative contents of different buffer solution on the antibody fixed on the surface of the vessel stent, example 5 makes the control of the relative contents of antibodies fixed with the holes under different craft conditions, and the steps thereof is as follows:

(1) immerging the vessel stent of 12 mm length which has holes into the phosphate buffer solution, whose pH is 7.2~7.4, or carbonate buffer solution, whose pH is 9.6, containing 0.1~10 μg/mL CD34 antibody such as type II mouse anti-human CD34 antibody produced by U.S. Stem Cell Technology Co., Ltd. to incubate for 30 min~2 h at 25~37° C. and then taking out the scaffold to dry in the air;

(2) determining the impact of different pH values on the relative contents of antibody fixed on the surface of the vessel stent with holes, and the result shown in FIG. 7 indicates that the relative contents of the antibody fixed on the vessel stent in the carbonate solution are more than that in other solutions under the same conditions.

INDUSTRIAL APPLICABILITY

The present invention provides a method for fixing antibody on the surface of medical instrument. The method can promote the firm degree of the antibody which is fixed on the surface of the instrument and keep high activity of the antibody on the surface of medical instrument. The practicality in industry thereof is shown as follows:

(1) It forms the surface with holes which have same size and the multicrystal phase structure in the surface of the medical instrument by chemical corrosion, electrochemical corrosion; the biological product antibody is fixed on the surface of the medical instrument by the effect of physical adsorption with a high firm degree for keeping high activity of the antibody on the surface of the medical instrument.

(2) The formation of the holes makes it possible to fix the biological product antibody on the surface of the medical instrument well and thus gives full play to the role of the biological products in the prevention of in-stent restenosis and antithrombotic and overcomes the negative impacts brought about by the medical instrument in the process of using, such as in-stent restenosis and formation of antithrombotic, to is bring gospel for patients with coronary atherosclerosis.

(3) The present invention has simple craft and accurate and reliable detection results and can be widely applied to biochip and the surface of the medical instrument, such as vessel stents and orthopedic implant devices, for fixing the biological antibody.

The invention claimed is:

1. A method for fixing an antibody on the surface of a medical instrument, characterized in that the method includes ① pre-treating the instrument surface, ② preparing holes, (3) post-treating the instrument surface and (4) fixing the antibody; first, preparing a multicrystal phase structure which has the same size holes in the surface of the instrument by chemical corrosion, electrochemical corrosion, anodic oxidation, micro-arc oxidation, or micro-arc nitridation; and then immersing the bare metal scaffold which has holes in the surface into a buffer solution containing the antibody, adjusting the pH value of the antibody buffer solution, fixing the antibody on the surface of the instrument by the attraction between positive and negative charge and hole effect; and finally, confirming the effectiveness of the fixed antibody by artificial simulation hemodynamics and detecting method of antibody activity on the scaffold surface.

2. The method for fixing an antibody on the surface of a medical instrument according to claim 1, characterized in that the step (1) pre-treating the instrument surface includes: washing the instrument surface by ultrasonication to remove impurities, using analytical reagent acetone solution at a concentration of 99.5% or medical ethanol solvent at a concentration of 75% to wash the scaffold body material for 5 to 15 minutes using 28 to 100 khz ultrasonication to remove the impurities on the body material, putting the washed body material in a dryer to dry at 30 to 40° C. for 30 to 60 minutes, and then taking out the body material for reservation.

3. The method for fixing an antibody on the surface of a medical instrument according to claim 1, characterized in that the step (2) preparing holes includes: directly preparing holes of the same size in the instrument by acid solution corrosion; immersing the instrument material into the corrosion solution at 0 to 100° C.; and the corrosion solution is preferably hydrochloric acid at a concentration of 1 to 38% or hydrochloric acid mixed acid solution containing 1 to 38% hydrochloric acid mixed with 1 to 98% vitriol; and then forming single nanometer-size holes after corrosion for 1 minute to 480 hours; the corrosion time varies according to the concentration and temperature.

4. The method for fixing an antibody on the surface of a medical instrument according to claim 1, characterized in that the step (3) post-treating the instrument surface includes: using 99.5% analytical reagent acetone solution and distilled water in sequence to wash the body material for 5 to 15 minutes using 28 to 100 khz ultrasonication; and finally putting the washed body material in a dryer to dry at 30 to 40° C. for 30 to 60 minutes, and then taking out the body material for reservation, or preparing 1 to 38% hydrochloric acid solution with distilled water and then immersing the body material into the prepared solution and putting the solution containing the body material into an incubator at 20° C. and then taking out the body material after 30 minutes to 48 hours.

5. The method for fixing an antibody on the surface of a medical instrument according to claim 1, characterized in that the instrument includes scaffold, catheter, guide wire, heart pacemakers, heart valves, surgical implant materials, implant hard tissue, and non-metal medical instrument whose substrate is ceramics, organic polymer, inorganic substance or metal oxide; the scaffold is balloon-expandable, self-expanding, vessel or non-vessel stent, stent whose substrate is stainless steel, nickel-titanium memory alloy, cobalt-based alloy, titanium or titanium alloy; and the scaffold made by wire weaving, tube laser cutting, die casting or welding.

6. The method for fixing an antibody on the surface of a medical instrument according to claim 1, characterized in that the biological product antibodies include one or more of the following substances: heparin, anti-platelet membrane glycoprotein (GPIIb/IIIa) receptor antagonists, antibody-treating cancer drug, abciximab, biological peptides, CD34 antibody, CD31 antibody and CD133 antibody.

7. The method for fixing an antibody on the surface of a medical instrument according to claim 1, characterized in that the step (4) fixing the antibody includes:
(1) immersing the scaffold which has holes in surface into the phosphate buffer solution or the carbonate buffer solution containing 0.1 to 100 μg/mL CD34 antibody to incubate for 20 to 60 minutes at 25 to 37° C. and then taking out the scaffold;
(2) washing the scaffold 3 times for 5 minutes per time using the phosphate buffer solution and blowing the scaffold for 15 minutes at room temperature and then preserving the scaffold at 4° C. after it becomes dry.

8. The method for fixing an antibody on the surface of a medical instrument according to claim 1, characterized in that conducting step (5) directly detecting the antibody activity after fixing the antibody includes: performing fluorescence coloring through the specific reaction of CD34 antigen-antibody using fluorescein isothiocyanate (FITC) labeled mouse anti-human CD34 antibody and detecting the antibody activity on the scaffold surface by photo-detection of fluorescence using fluorescence microscope.

9. The method for fixing an antibody on the surface of a medical instrument according to claim 1, characterized in that after the step (4) fixing the antibody, step (6) indirectly detecting the antibody activity is conducted: detecting the antibody activity on the scaffold surface using 3-amino-9-ethyl-carbazole (AEC) staining kit after the antibody is cascade amplified by horseradish peroxidase (HRP) labeled goat anti-mouse IgG secondary antibody.

10. The method for fixing an antibody on the surface of a medical instrument according to claim 1 is characterized in that after the step (4) fixing the antibody, step (7) detecting the content of the antibody on surface is conducted: indirectly detecting the content of the antibody on the scaffold surface by tetramethylbenzidine (TMB) chromogenic after cascade amplification of goat anti-mouse IgG secondary antibody labeled by horseradish peroxidase (HRP); the steps are as follows:
(1) immersing the scaffold with antibody on surface into the phosphate buffer solution containing 500 μL of 5 to 10% bovine serum albumin (BSA) to incubate at 25 to 37° C. for 30 minutes to 2 hours and then taking out the scaffold to dry in the air;
(2) immersing the scaffold into the phosphate buffer solution containing horseradish peroxidase (HRP) labeled goat anti-mouse IgG to incubate at 25 to 37° C. for 20 to 30 minutes and then taking out the scaffold;
(3) washing the scaffold 3 times for 5 minutes per time with the phosphate buffer solution; putting the scaffold into 500 μL TMB substrate buffer solution; the 500 μL TMB substrate buffer solution is made of, such as, 0.5 mL anhydrous ethanol of 10 mg/5 mL mixed with 5 mL substrate buffer solution; the substrate buffer solution is made of, such as, 1.42 g $Na_2HPO_4$ mixed with 0.96 g sodium citrate which is added distilled water to 50 mL; after washing, adding 32 μL hydrogen peroxide of 0.75% into the phosphate buffer solution to incubate for 15 minutes and then adding 250 μL 2 M sulfuric acid solution to terminate the reaction;
(4) using a microplate reader to measure the absorbance of the solution at 492 nm; coating CD34 antibody having a known concentration on an ELISA plate according to the different concentration gradients of 1:10, 1:20, 1:50, 1:100, 1:500, 1:1000, and 1:10000, and then drawing a standard curve by simulation of the concentration of CD34 antibody with A492 nm;

(5) determining the amount of the antibody on the scaffold surface according to the measured absorbance and the standard curve; the result showed that 316L stainless steel stent with holes can fix 1 to 20 ng CD34 antibody each 1 mm in length.

11. The method for fixing an antibody on the surface of a medical instrument according to claim 1, characterized in that after the step ④ fixing the antibody, step ⑧ detecting the firmness of the antibody is conducted: putting the scaffold that has the fixed mouse anti-human CD34 antibody on surface into fluid artificial simulated body fluid, such as the phosphate buffer solution whose pressure is 100 mmHg and flow rate is 91 cm/s, performing a scouring experiment, when the scaffold is in a normal state or in a state after the balloon dilation; finally, using the method described in step ⑥ to detect the antibody activity on the scaffold surface and using the method of step ⑦ to quantify the antibody on the scaffold.

* * * * *